US012201687B2

(12) United States Patent
Falo, Jr. et al.

(10) Patent No.: US 12,201,687 B2
(45) Date of Patent: Jan. 21, 2025

(54) COMPOSITIONS FOR MODULATING AN XBP1 PATHWAY IN A KERATINOCYTE AND METHODS OF USE

(71) Applicant: UNIVERSITY OF PITTSBURGH-OF THE COMMONWEALTH SYSTEM OF HIGHER EDUCATION, Pittsburgh, PA (US)

(72) Inventors: Louis D. Falo, Jr., Wexford, PA (US); Zhaoyang You, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 312 days.

(21) Appl. No.: 17/558,977

(22) Filed: Dec. 22, 2021

(65) Prior Publication Data
US 2022/0218821 A1 Jul. 14, 2022

Related U.S. Application Data

(63) Continuation of application No. 15/738,612, filed as application No. PCT/US2016/039265 on Jun. 24, 2016, now abandoned.

(60) Provisional application No. 62/184,287, filed on Jun. 25, 2015.

(51) Int. Cl.
A61K 48/00 (2006.01)
A61K 9/00 (2006.01)
A61K 39/00 (2006.01)
A61K 39/02 (2006.01)
A61K 39/12 (2006.01)
A61K 39/39 (2006.01)
C07K 14/47 (2006.01)
A61K 38/00 (2006.01)

(52) U.S. Cl.
CPC ............ A61K 39/39 (2013.01); A61K 9/0014 (2013.01); A61K 39/0011 (2013.01); A61K 39/02 (2013.01); A61K 39/12 (2013.01); A61K 48/00 (2013.01); C07K 14/47 (2013.01); A61K 38/00 (2013.01); A61K 2039/54 (2013.01); A61K 2039/55516 (2013.01)

(58) Field of Classification Search
None
See application file for complete search history.

(56) References Cited

U.S. PATENT DOCUMENTS

2006/0063187 A1    3/2006    Hotamisligil et al.

FOREIGN PATENT DOCUMENTS

WO    2004/111194 A2    12/2004
WO    2010/008860 A1    1/2010

OTHER PUBLICATIONS

Zhang, Yi et al. "Genetic Vaccines to Potentiate the Effective CD103+ Dendritic Cell-Mediated Cross-Priming of Antitumour Immunity", The Journal of Immunology, vol. 194, pp. 5937-5947, 2015.
International Search Report and Written Opinion mailed Aug. 24, 2016, from International Application No. PCT/US2016/039265, 12 pages.
Tian, S. et al.; Genetic Targeting of the Active Transcription Factor XBP1s to Dendritic Cells Potentiates Vaccine-Induced Prophylactic and Therapeutic Antitumor Immunity; Molecular Ther., 2012, vol. 20; 11 pages.
Gaffal, E. et al.; Comparative evaluation of CD8+CTL responses following gene gun immunization tageting the skin and intracutaneous injection of antigen-transduced dendritic cells; European J. Cell Biology, 2007, vol. 86; 10 pages.
Condon et al.; DNA-based immunization by in vivo transfection of dentrictic cells; Nature Med., 1996, vol. 2.; 7 pages.
Tuting, T et al.; J. Investigative Dermatology, 1998, vol. 111: pp. 183-188.
Ono, et al., "Human X-box-binding protein 1 is required for the transcription of a subset of human class II major histocompatibility genes and forms a heterodimer with c-fos", National Academy of Sciences of the United States of America. 88 (10): 4309-12) (1991).
Zeng, et al., "Vascular endothelial cell growth-activated XBP1 splicing in endothelial cells is crucial for angiogenesis", Circulation. 127 (16): 1712-22) (2013).
Bettigole, et al., "The transcription factor XBP1 is selectively required for eosinophil differentiation". Nature Immunology. 16 (8): 829-37) (2015).

Primary Examiner — Michael D Burkhart
(74) Attorney, Agent, or Firm — Meunier Carlin & Curfman LLC

(57) ABSTRACT

Provided herein are compositions and methods for increasing an immune response in a subject, immunizing a subject and/or treating a disease in a subject that relate to keratinocytes. It is a surprising finding of the present invention that modulation of an XBP1 pathway creates a keratinocyte that is itself an immune modulator, or adjuvant. In some embodiments, the concentration of antigen is increased in the vicinity of the keratinocyte, further increasing the immune response by effector cells within that vicinity.

21 Claims, 19 Drawing Sheets

Specification includes a Sequence Listing.

Fig. 1(A-B)
A.
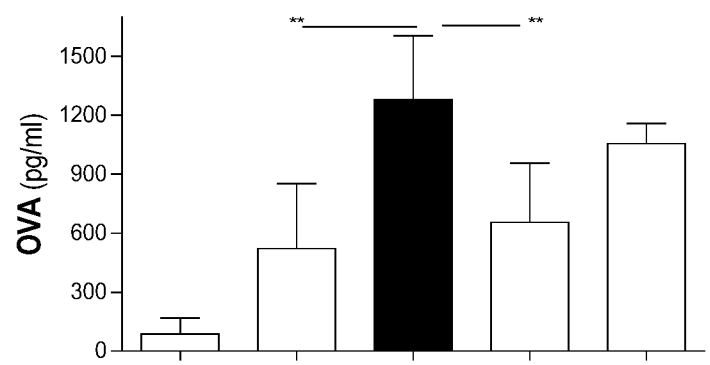
B.
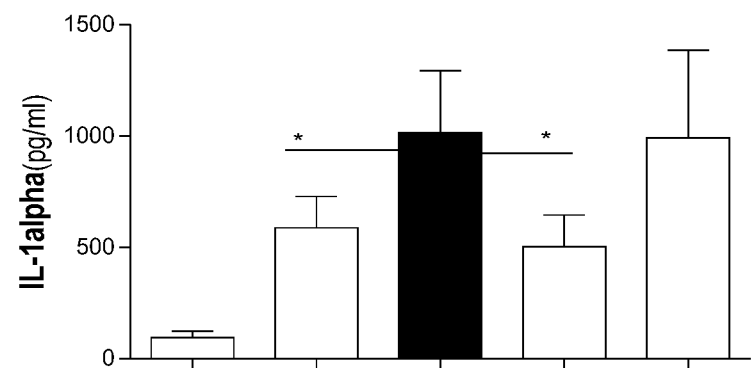

Fig. 1(C-D)
C.
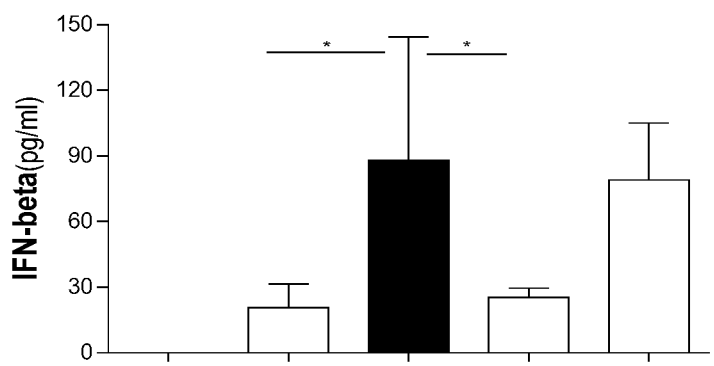
D.
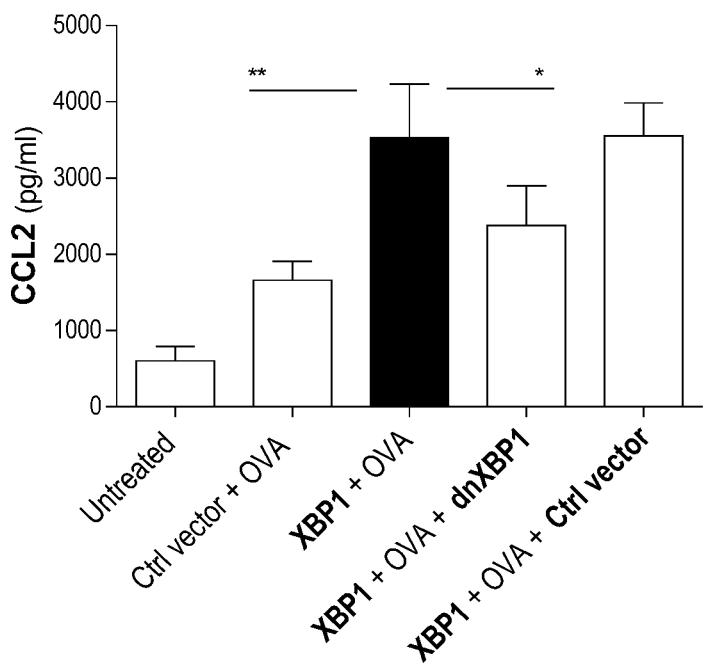

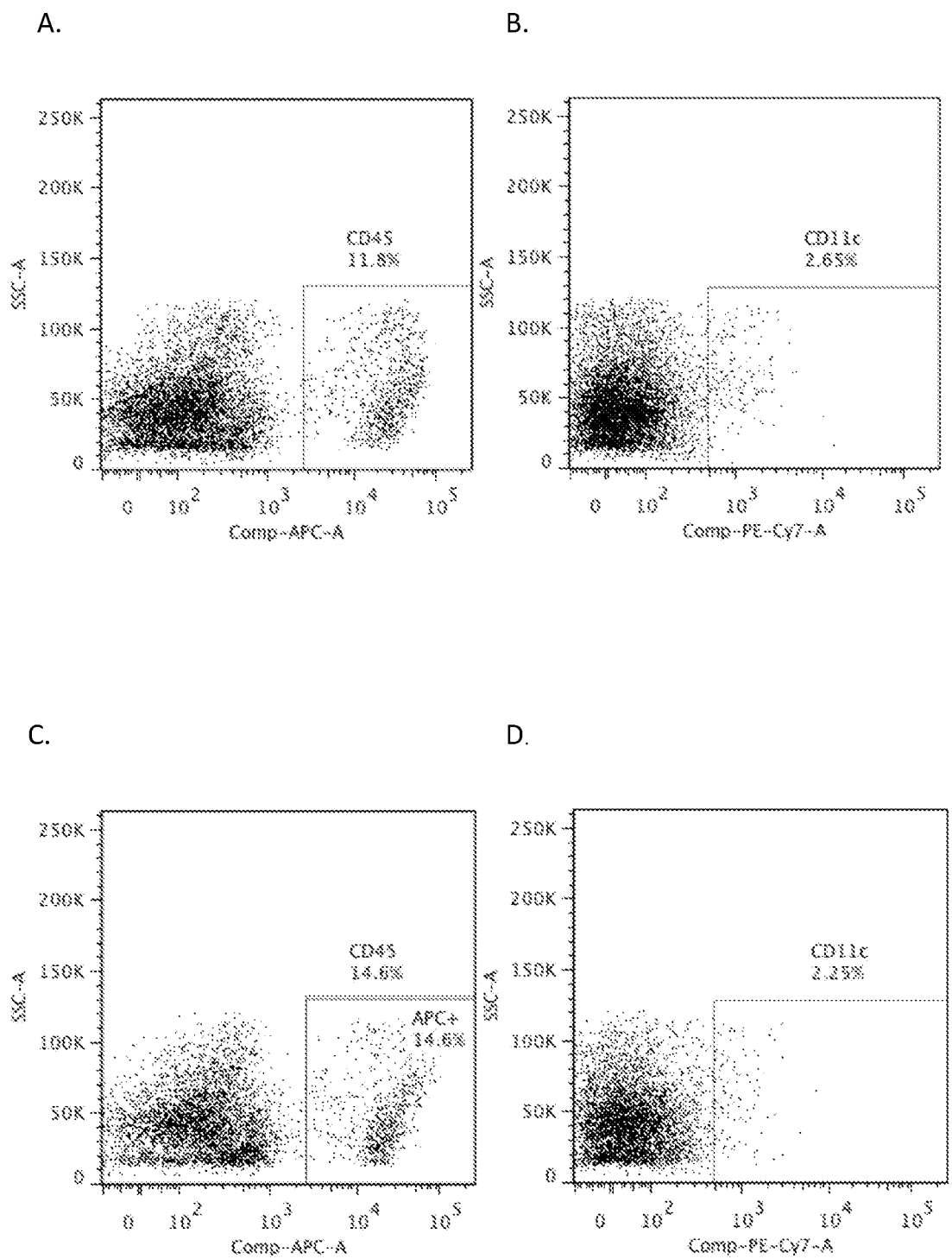
Fig. 2(A-D)

E.
F.
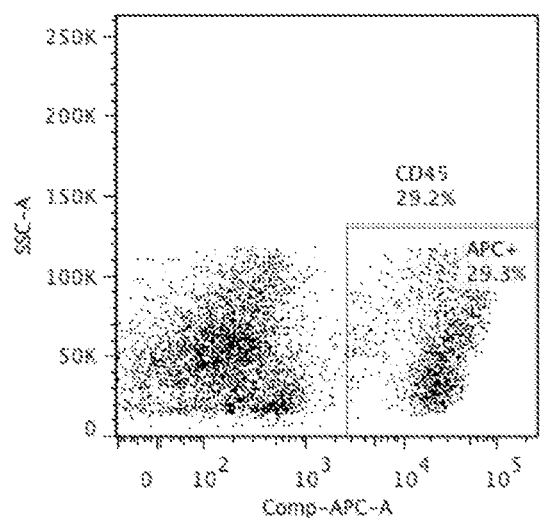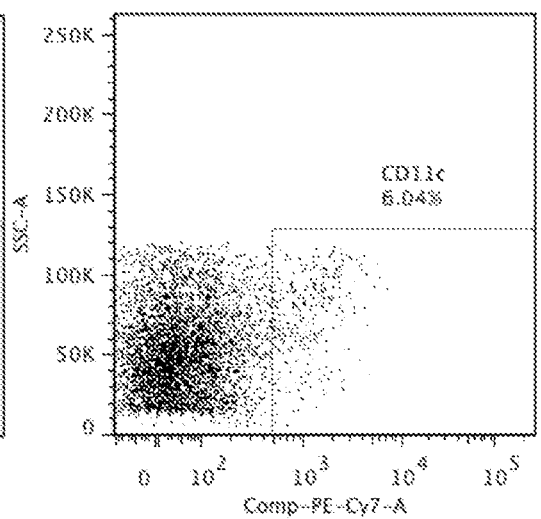
Fig. 2(E-F)

Fig. 3(A-B)
A.
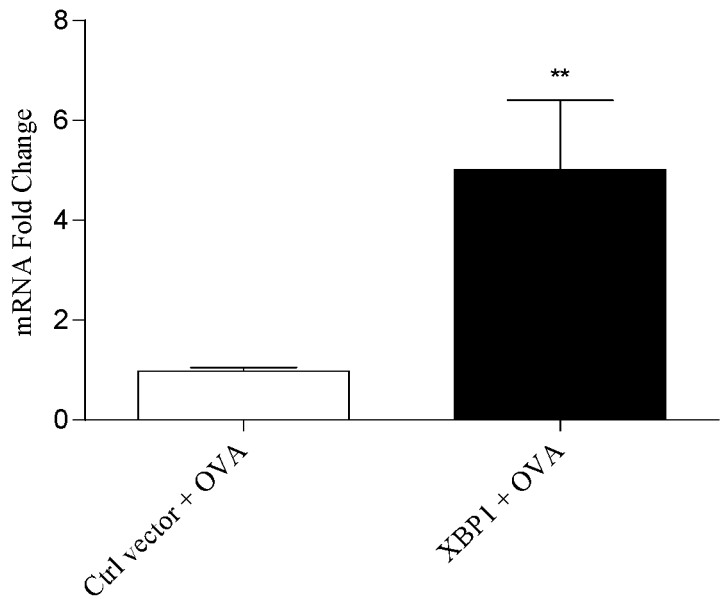
B.
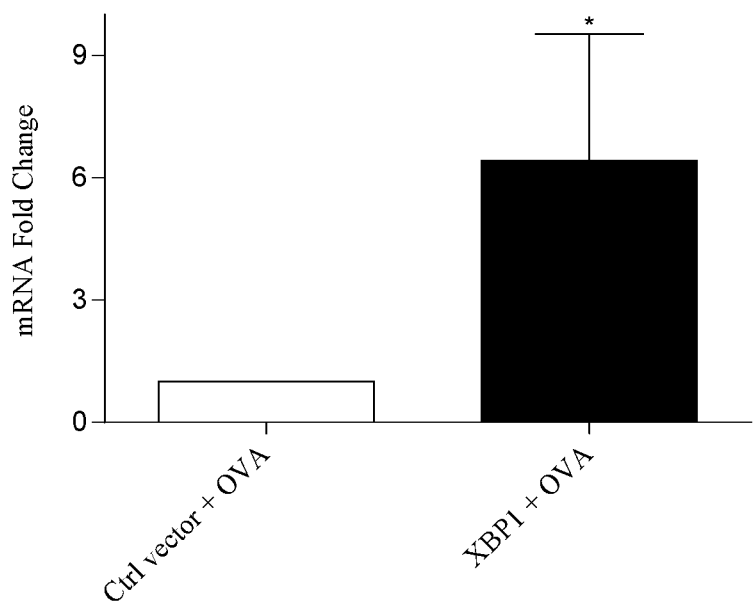

Fig. 3(C-D)
C.
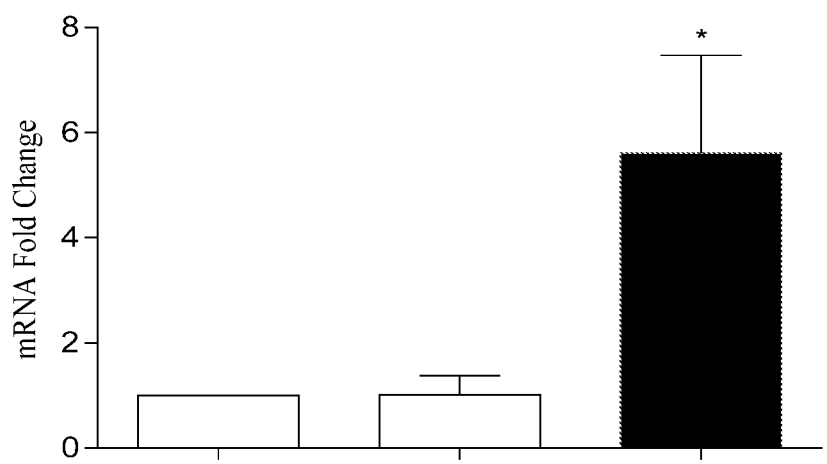
D.
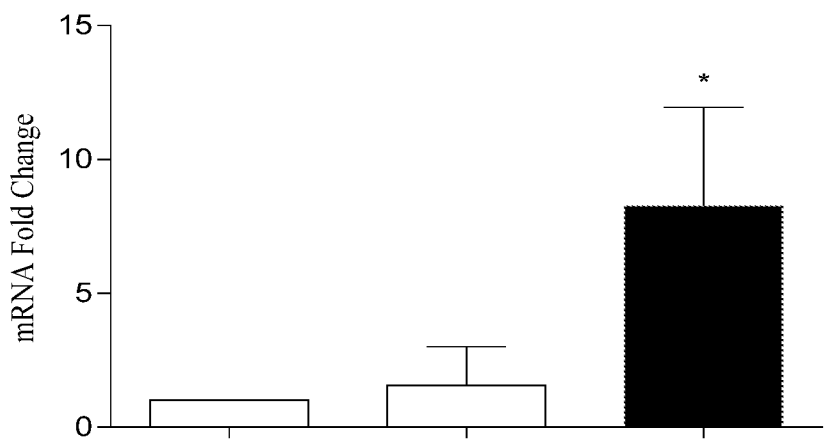

Fig. 3(E-F)
E.
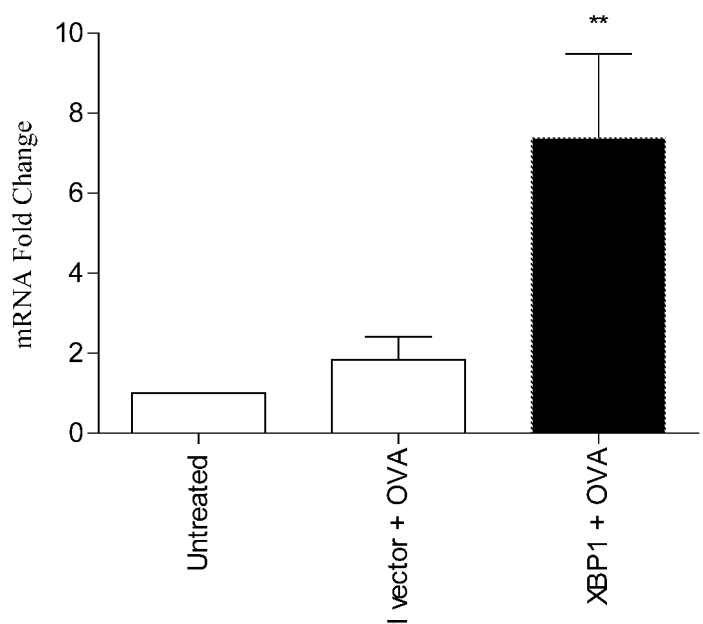
F.
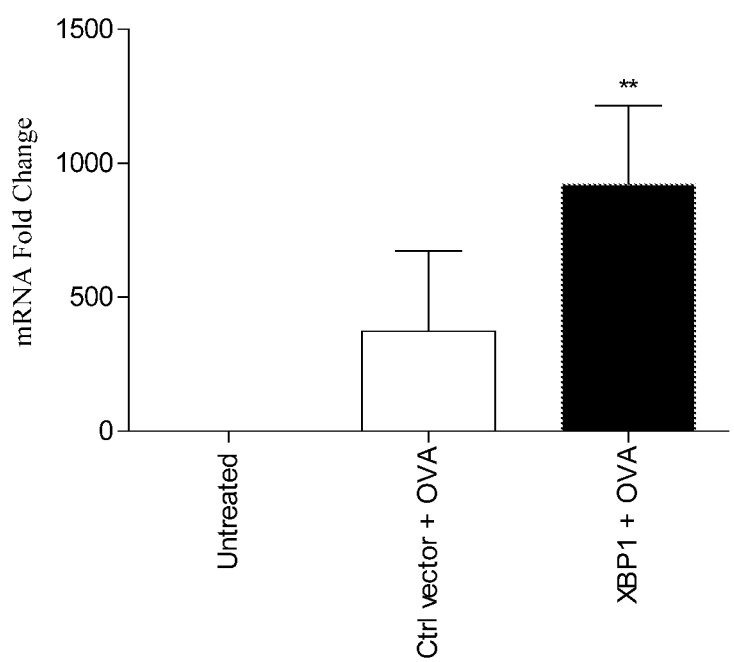

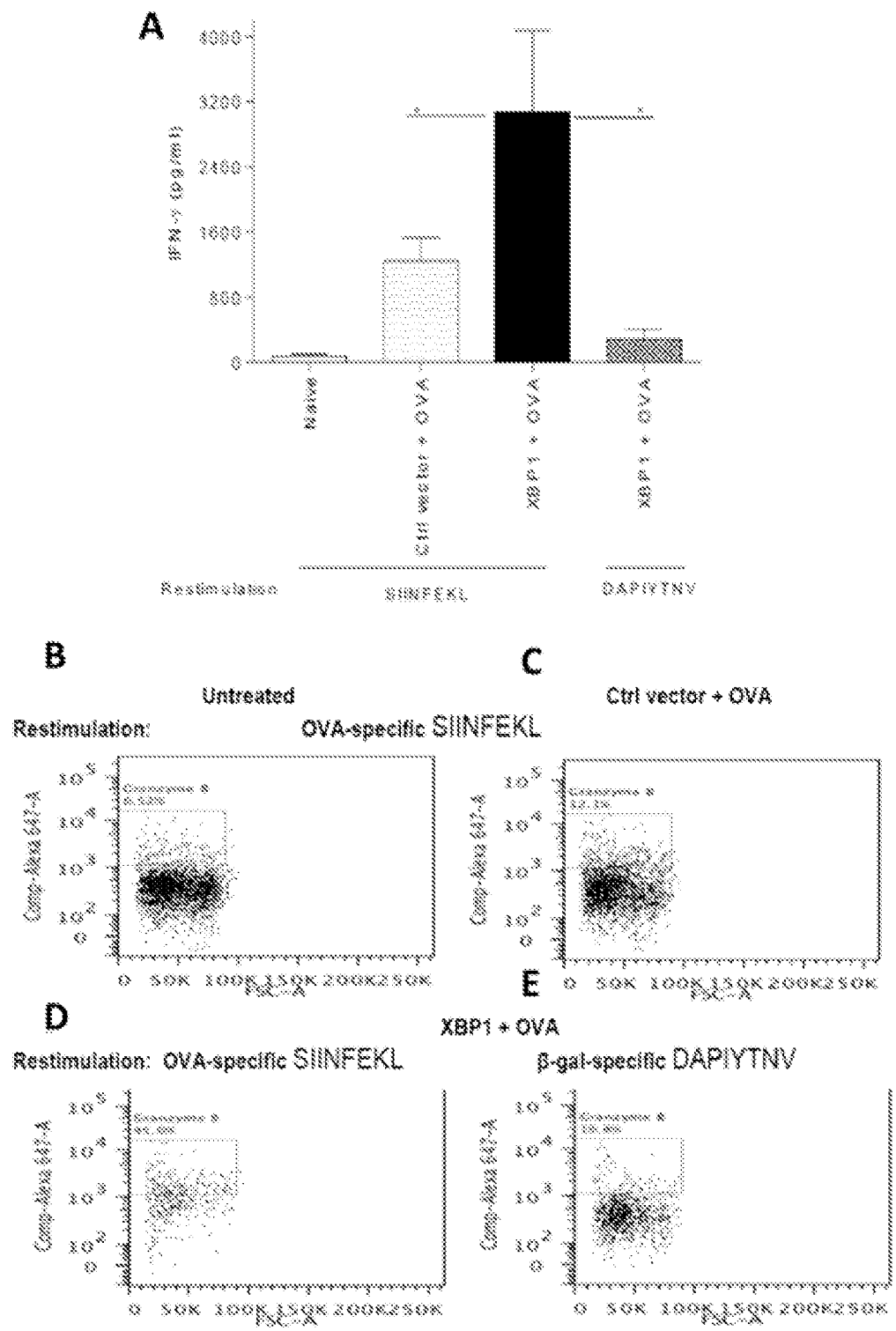
Fig. 4(A-E)

A.
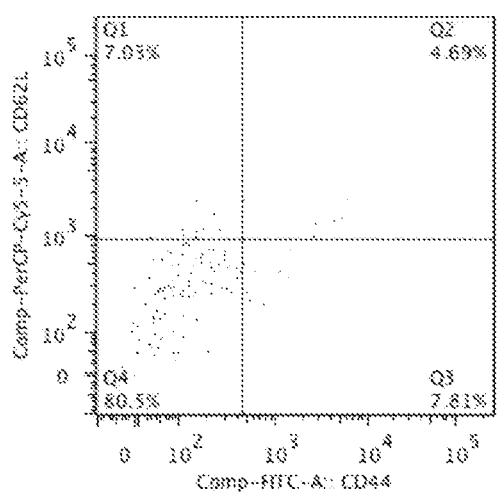
B.
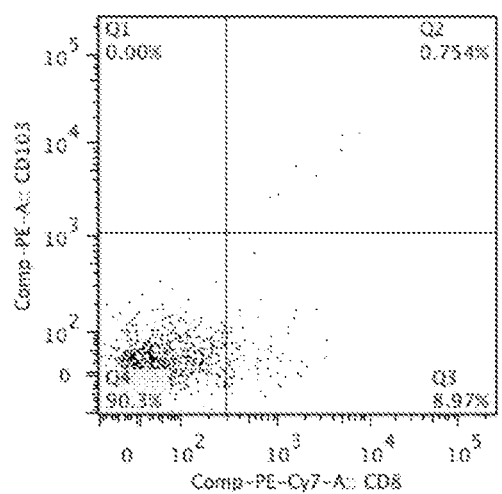
C.
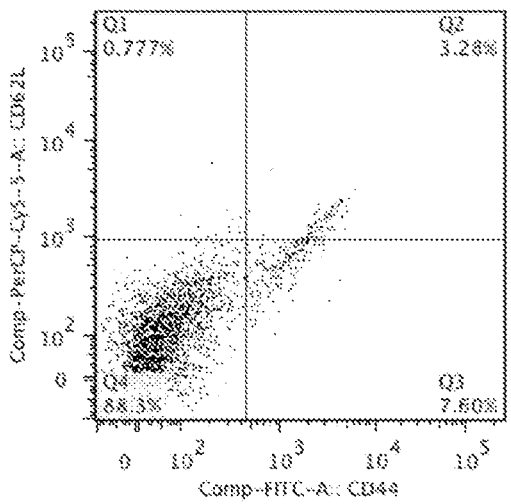
D.
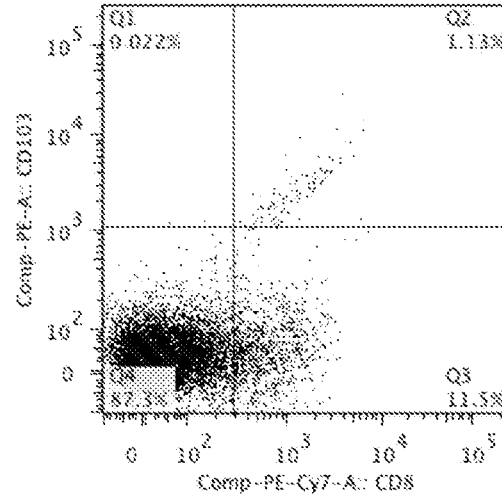
Fig. 5(A-D)

E.
F.
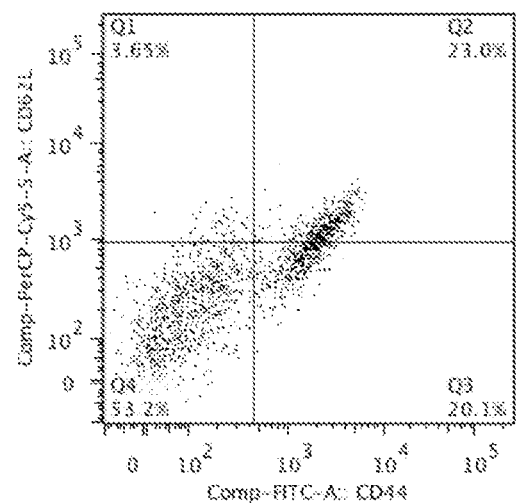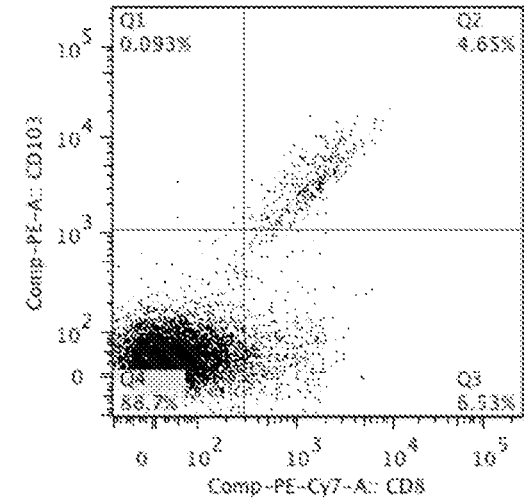
Fig. 5(E-F)

Fig. 6(A-B)
A.
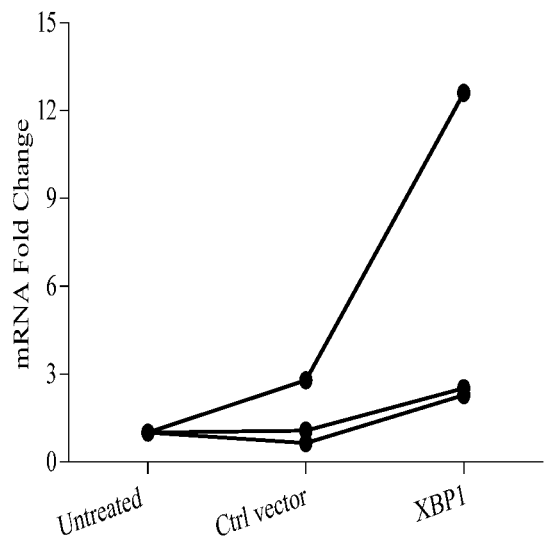
B.
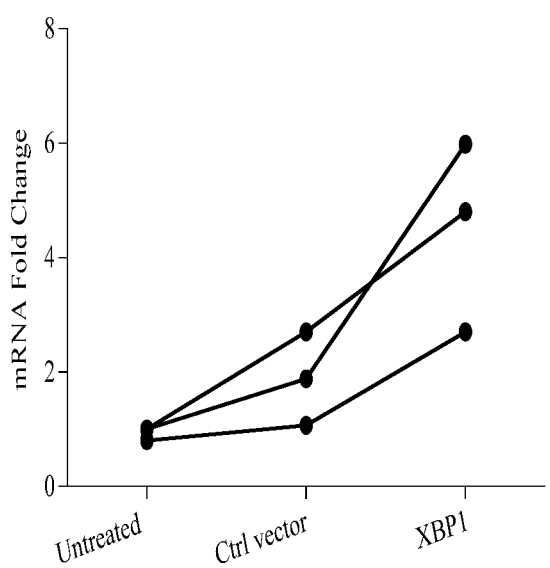

Fig. 6(C-D)
C.
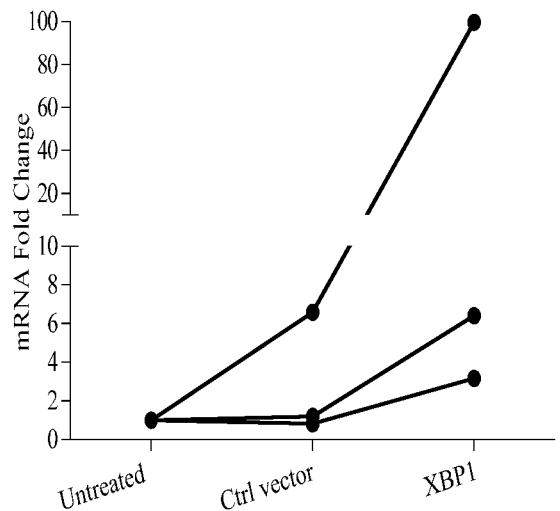
D.
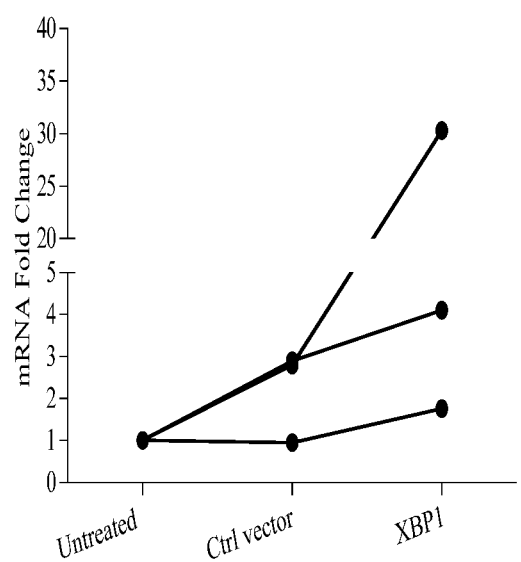

Fig. 6(E-F)
E.
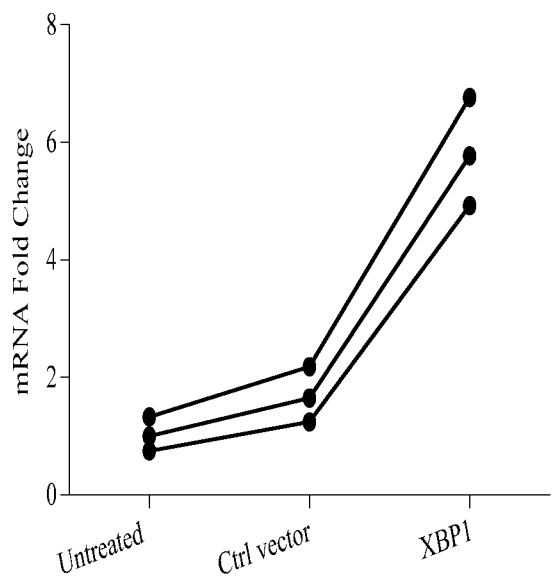
F.
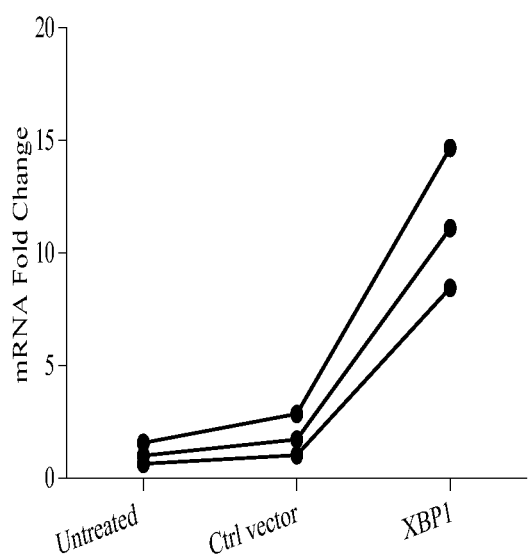

Fig. 6(G-H)
G.
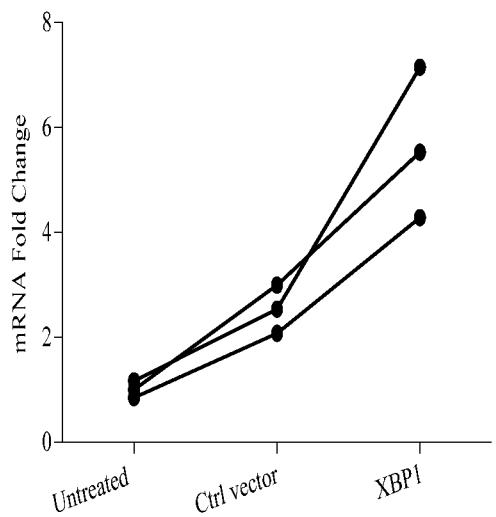
H.
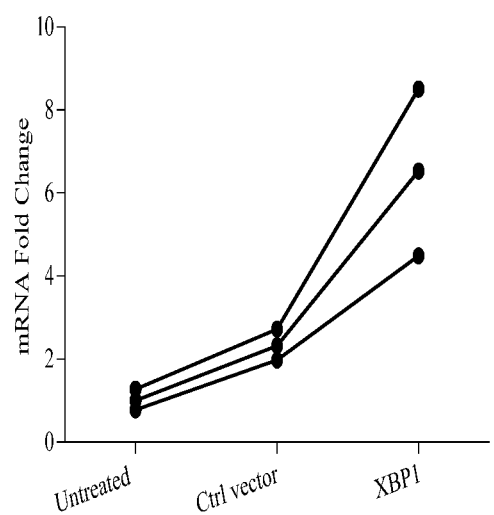

Fig. 6(I-J)
I.
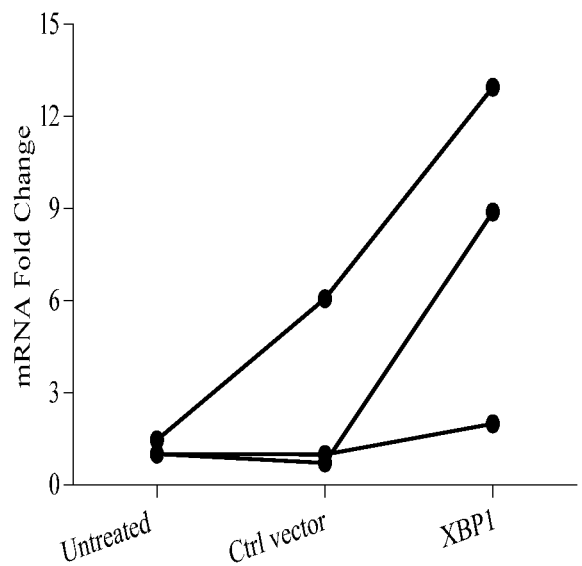
J.
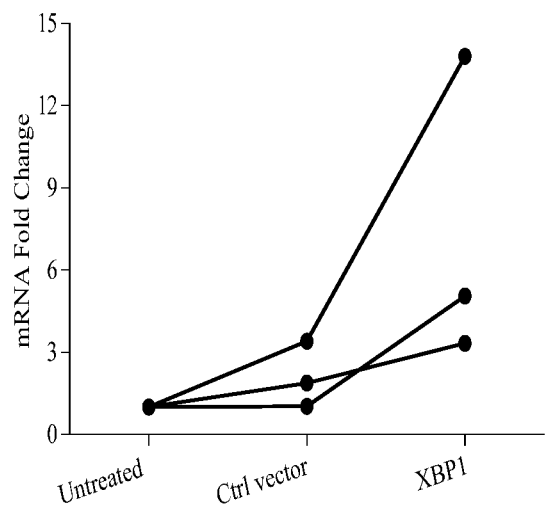

Fig. 6(K-L)
K.
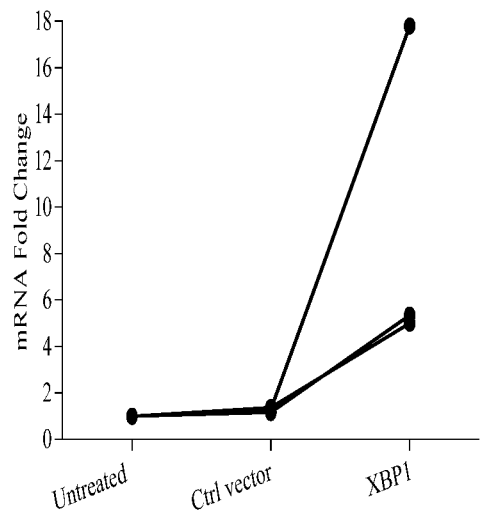
L.
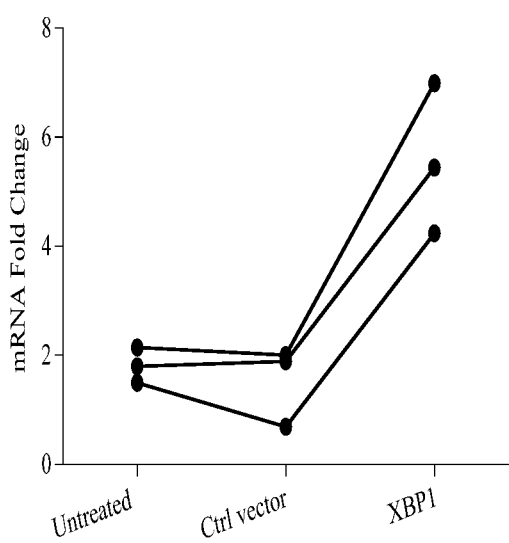

Fig. 6(M-N)
M.
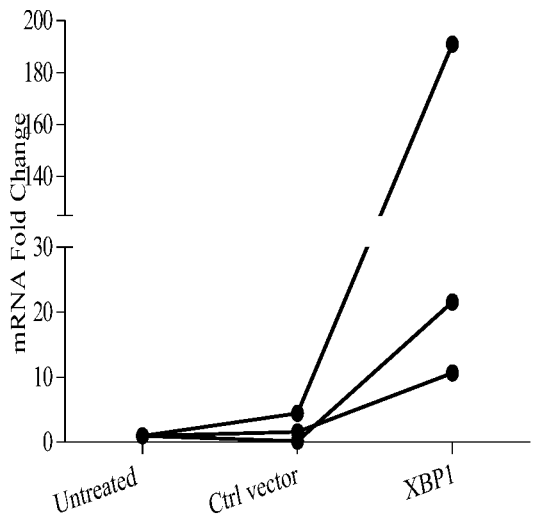
N.
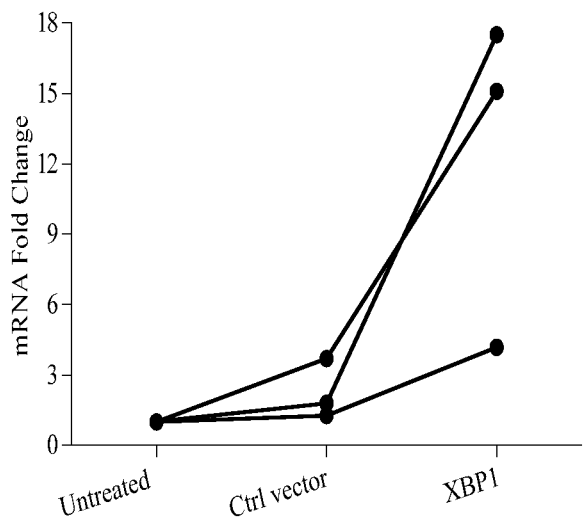

O.

COMPOSITIONS FOR MODULATING AN XBP1 PATHWAY IN A KERATINOCYTE AND METHODS OF USE

CROSS-REFERENCE TO RELATED APPLICATIONS

This application is a continuation of U.S. application Ser. No. 15/738,612, which is a 371 of International Application Number PCT/US2016/039265, filed Jun. 24, 2016, which claims the priority benefit of U.S. Provisional Application No. 62/184,287, filed Jun. 25, 2015, which are hereby incorporated herein by reference in their entirety.

REFERENCE TO SEQUENCE LISTING

The Sequence Listing submitted Dec. 22, 2021, as a text file named "10504-004US2 2021_12_22 Sequence Listing.txt," created on Jun. 24, 2016, and having a size of 111 bytes is hereby incorporated by reference pursuant to 37 C.F.R. § 1.52(e)(5).

BACKGROUND OF THE INVENTION

1) Field of the Invention

The field of the invention is immunology.

2) Description of Related Art

The skin can be a uniquely immunogenic target for immunization, as it contains an extensive array of immunologically responsive cell types that contribute to both innate and adaptive immunity. Strategic engineering of the skin to create a pro-immunogenic microenvironment could lead to more effective preventive and therapeutic vaccines against dreaded diseases such as cancer and AIDS.

The transcription factor x-box binding protein 1 (spliced) XBP1, which is an endoplasmic reticulum (ER)-stress associated factor regulating ER structure and function, can promote the production and secretion of proteins, and regulate cell differentiation and survival in certain cells. However, the regulatory networks affected by XBP1 are not well understood.

BRIEF DESCRIPTION OF THE DRAWINGS

FIG. 1(A-D) contains graphs showing XBP1 enhances the production of secreted vaccine antigen and pro-inflammatory cytokines by keratinocytes. OVA (FIG. 1A), IL-1α (FIG. 1B), IFN-β (FIG. 1C), CCL2 (FIG. 1D).

FIG. 2(A-F) contains graphs showing that XBP1 promotes lymphocyte and CD11c$^+$ cell infiltration into skin. FIG. 2A-B, untreated. FIG. 2C-D, Control vector+OVA. FIG. 2E-F, XBP1+OVA.

FIG. 3(A-F) contains graphs showing that XBP1 in vivo increases the expression of pro-inflammatory cytokines and chemokines and co-delivered vaccine antigen transgene. XBP1 (FIG. 3A), OVA (FIG. 3B), CCL2 (FIG. 3C), TNF-α (FIG. 3D), IL-1α (FIG. 3E), IL-1β (FIG. 3F).

FIG. 4(A-E) contains graphs showing that XBP1 overexpression enables induction of durable systemic antigen-specific IFN-γ- and Granzyme B-expressing CD8$^+$ T cell immunity. FIG. 4A showing the levels of IFN-γ in the culture supernatants determined by ELISA. FIG. 4B showing untreated, restimulation with OVA-specific SIINFEKL. FIG. 4C showing control vector+OVA, restimulation with OVA-specific SIINFEKL. FIG. 4D showing XBP1+OVA, restimulation with OVA-specific SIINFEKL, FIG. 4E showing XBP1+OVA, restimulation with β-gal-specific DAPIYTNV.

FIG. 5(A-F) contains graphs showing that XBP1 promotes the accumulation of memory [central (CD44$^+$CD62L$^+$) and effector (CD44$^+$CD62L$^-$)] CD8$^+$ T cells and skin-resident CD103$^+$CD8$^+$ memory T cells in skin at the immunization site. FIG. 5A-B, untreated. FIG. 5C-D, Control vector+OVA. FIG. 5E-F, XBP1+OVA.

FIG. 6(A-O) contains graphs showing that overexpression of XBP1 in situ (FIG. 6A) triggers expression of known XBP1 responsive genes (GRP78, GFAT-1 and VEGFA; FIGS. 6B, 6C, 6D), and genes associated with keratinocytes migration, proliferation and function (HIF-1α FIG. 6E), pro-inflammatory responses (IL-23α, S100A7, IL-1β, MyD88, OAS1, TNF-α; FIGS. 6F, 6G, 6I, 6K, 6N), the recruitment and activation of immunocytes (CCL19, CD86 and IL-15; FIGS. 6H, 6L, 6M), and co-delivered vaccine antigen transgene (OVA.

DETAILED DESCRIPTION OF THE INVENTION

Figure 6O:
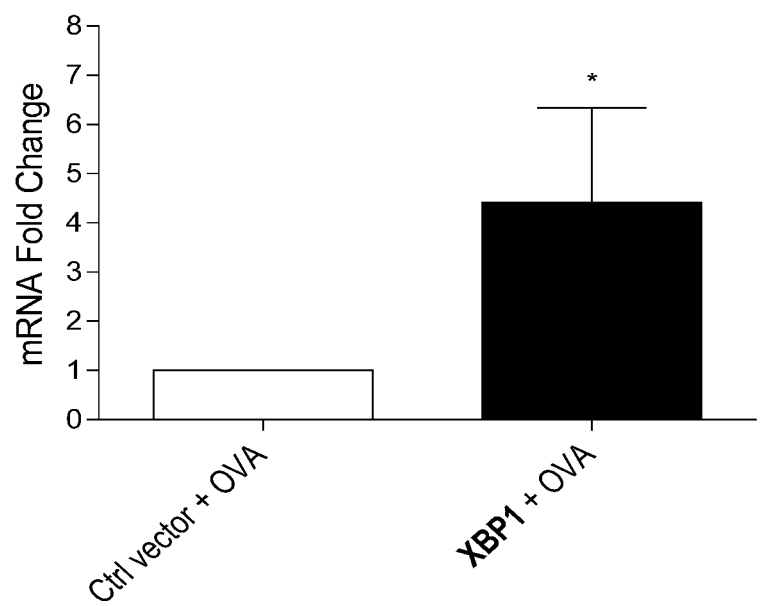
FIG. 6O).

Provided herein are compositions and methods for increasing an immune response in a subject, immunizing a subject and/or treating a disease in a subject that relate to keratinocytes. Terms used throughout this application are to be construed with ordinary and typical meaning to those of ordinary skill in the art. However, Applicant desires that the following terms be given the particular definition as defined below.

Definitions

As used in the specification and claims, the singular form "a," "an," and "the" include plural references unless the context clearly dictates otherwise. For example, the term "a cell" includes a plurality of cells, including mixtures thereof.

The term "administering" refers to an administration that is oral, topical, intravenous, cutaneous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques. In one embodiment, the administration is cutaneous or transdermal. It should be understood that a cutaneous administration does not require systemic delivery of the administered composition.

The terms "about" and "approximately" are defined as being "close to" as understood by one of ordinary skill in the art. In one non-limiting embodiment, the terms are defined to be within 10%. In another non-limiting embodiment, the terms are defined to be within 5%. In still another non-limiting embodiment, the terms are defined to be within 1%.

The term "antigen" refers to any composition toward which an immune response is generated. Antigens include, but are not limited to, polypeptides, oligopeptides, and polysaccharides. In one embodiment, the antigen is a polypeptide.

The terms "cell," "cell line," and "cell culture" include progeny. It is also understood that all progeny may not be precisely identical in DNA content, due to deliberate or inadvertent mutations. Variant progeny within a population, which population has the same overexpression of XBP1 as screened for in the originally engineered cell population, are included.

A "composition" is intended to include a combination of active agent or agents (for example, an XBP1 pathway upregulating composition) and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

The term "disease" refers to an abnormal condition of a part, organ, or system of a subject resulting from various causes, such as infection, inflammation, environmental factors, or genetic defect, and characterized by an identifiable group of signs, symptoms, or both. In some embodiments, the disease is a cancer.

An "effective amount" is an amount sufficient to effect beneficial or desired results. An effective amount can be administered in one or more administrations, applications or dosages.

As used herein, "gene expression" and "protein expression" refer to the process by which polynucleotides are transcribed into mRNA and the process by which the transcribed mRNA is subsequently being translated into peptides, polypeptides, or proteins, respectively. If the polynucleotide is derived from genomic DNA, expression may include splicing of the mRNA in a eukaryotic cell. "Gene overexpression" refers to the overproduction of the mRNA transcribed from the gene, at a level that is about 2.5 times higher, about 5 times higher, or about 10 times higher than the expression level detected in a control sample. "Protein overexpression" includes the overproduction of the protein product encoded by a gene at a level that is about 2.5 times higher, about 5 times higher, or about 10 times higher than the expression level detected in a control sample.

As used herein "surface expression" refers to the process by which polypeptides are translocated to the surface of a cell such that at least a portion of the polypeptide is located at the exterior of the cell surface. "Surface overexpression" includes an increase in the amount of a particular polypeptide at the exterior surface of a cell, at a level that is about 2.5 times higher, about 5 times higher, or about 10 times higher than the surface expression level detected in a control sample.

A "gene" refers to a polynucleotide containing at least one open reading frame that is capable of encoding a particular polypeptide or protein after being transcribed and translated.

Any of the polynucleotides sequences described herein may be used to identify larger fragments or full-length coding sequences of the gene with which they are associated. Methods of isolating larger fragment sequences are known to those of skill in the art.

"Homologs" are defined herein as two polynucleotides or two polypeptides that have identity or homology. Homologs include allelic variants, orthologs, and paralogs having the same relevant function (e.g., ability to upregulate the XBP1 pathway). In some embodiments, homologs have about 99%, 98%, 97%, 96%, 95%, 94%, 93%, 92, 91% or 90% homology. In other embodiments, homologs have about 80% or about 85% homology.

The term "identity" or "homology" shall be construed to mean the percentage of nucleotide bases or amino acid residues in the candidate sequence that are identical with the bases or residues of a corresponding sequence to which it is compared, after aligning the sequences and introducing gaps, if necessary to achieve the maximum percent identity for the entire sequence, and not considering any conservative substitutions as part of the sequence identity. Neither N- nor C-terminal extensions nor insertions shall be construed as reducing identity or homology. A polynucleotide or polynucleotide region (or a polypeptide or polypeptide region) that has a certain percentage (for example, 80%, 85%, 90%, or 95%) of "sequence homology" to another sequence means that, when aligned, that percentage of bases (or amino acids) are the same in comparing the two sequences. This alignment and the percent homology or sequence identity can be determined using software programs known in the art. In one embodiment, default parameters are used for alignment. In one embodiment a BLAST program is used with default parameters. In one embodiment, BLAST programs BLASTN and BLASTP are used with the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

The term "immunizing" refers to increasing an antigen-specific immune response in a subject.

The term "keratinocyte" refers to an epidermal cell that expresses one or more keratin polypeptides. The term "keratinocyte" includes keratinocytes at each stage of differentiation, but does not include corneocytes. In some embodiments, the keratinocyte expresses or overexpresses a keratin-5 polypeptide and a keratin-14 polypeptide. In other embodiments, the keratinocyte expresses or overexpresses a keratin-1 polypeptide and a keratin-10 polypeptide. In still other embodiments, the keratinocyte expresses or overexpresses a keratin-1 polypeptide and a keratin-16 polypeptide.

"Mammal" for purposes of treatment refers to any animal classified as a mammal, including human, domestic and farm animals, nonhuman primates, and zoo, sports, or pet animals, such as dogs, horses, cats, cows, etc.

As used herein, the terms "neoplastic cells," "neoplasia," "tumor cells," "tumor," "cancer," and "cancer cells" (used interchangeably) refer to cells which exhibit relatively autonomous growth, so that they exhibit an aberrant growth phenotype characterized by a significant loss of control of cell proliferation (i.e., de-regulated cell division). Tumor cells can be malignant or benign. A metastatic cell or tissue means that the cell can invade and destroy neighboring body structures. In some embodiments, the cancer is a skin cancer such as a melanoma, a basal cell carcinoma or a squamous cell carcinoma.

A "pharmaceutical composition" is intended to include the combination of an active agent with a pharmaceutically acceptable carrier, inert or active, making the composition suitable for diagnostic or therapeutic use in vivo or ex vivo.

The term "pharmaceutically acceptable carrier" means a carrier or excipient that is useful in preparing a pharmaceutical composition that is generally safe and non-toxic, and includes a carrier that is acceptable for veterinary and/or human pharmaceutical use. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below. The pharmaceutical compositions also can include preservatives. A "pharmaceutically acceptable carrier" as used in the specification and claims includes both one and more than one such carrier.

The terms "pharmaceutically effective amount," "therapeutically effective amount," or "therapeutically effective dose" refer to the amount of a composition such as an XBP1 pathway upregulating composition, and optionally, antigen polynucleotide, that will elicit the biological or medical response of a tissue, system, animal, or human that is being sought by the researcher, veterinarian, medical doctor or other clinician. In some embodiments, a desired response is a treatment of a disease such as a bacterial infection, a viral infection or a cancer such as a skin cancer. In some instances, a desired biological or medical response is achieved following administration of multiple dosages of the composition to the subject over a period of days, weeks, or years. The terms "pharmaceutically effective amount," "therapeutically effective amount," or "therapeutically effective dose" include that amount of a composition such as a XBP1 pathway upregulating composition, and optionally, antigen polynucleotide, that, when administered, is sufficient to prevent development of, or alleviate to some extent, one or more of the symptoms of the disease being treated. The therapeutically effective amount will vary depending on the composition such as the a XBP1 pathway upregulating composition, and optionally, antigen polynucleotide, the disease and its severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of a XBP1 pathway upregulating composition, and optionally, antigen polynucleotide, includes an amount that is sufficient to prevent development of, suppress the growth of, or reduce the numbers of, one or more skin cancer lesions.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form. As used herein, an "antigen polynucleotide" is a polynucleotide that encodes a corresponding antigen polypeptide.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

"Suppress" tumor growth indicates a curtailment of growth state when compared to growth without contact with a XBP1 pathway upregulating composition and antigen polynucleotide described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

The terms "treat," "treating," "treatment" and grammatical variations thereof as used herein, include partially or completely delaying, alleviating, mitigating or reducing the intensity of one or more attendant symptoms of a disease and/or alleviating, mitigating or impeding one or more causes of a disease. Treatments according to the invention may be applied preventively, prophylactically, palliatively or remedially. Prophylactic treatments are administered to a subject prior to onset (e.g., before obvious signs of disease), during early onset (e.g., upon initial signs and symptoms of disease), or after an established development of disease. Prophylactic administration can occur for several days to years prior to the manifestation of symptoms of an infection. In some instances, the terms "treat," "treating," "treatment" and grammatical variations thereof, include partially or completely reducing the size of a solid tumor or cancer lesion or reducing the number of solid tumors or cancer lesions as compared with prior to treatment of the subject or as compared with the incidence of such symptom in a general or study population.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. A plasmid is the most commonly used form of vector, however, the invention is intended to include such other forms of vectors which serve equivalent function as and which are, or become, known in the art.

The term "XBP1 pathway upregulating composition" refers herein to any composition that when administered to a keratinocyte, increases or activates a constituent in an XBP1 regulated/responsive pathway. For example, downstream pathways known to be effected by XBP1 include those of the ER stress Gene Network including, for example, Sec24c, Sec31a, Sec23b, Sec24d, Sec61a1, Copg1, Copb2, Gosr2, Golgb1, Golga3, Arfgap3, Rpn2, Spcs3, Fasn, Hspa13, Surf4, Jnk, Mfn2, Atf6, Dnajc3, Pdia6, Pdia5, Pdia4, Rpn1, Os9, Hyou1, Csdc47, Stt3a, and Nlrx1. Other downstream pathways known to be effected by XBP1 include: Protein transport pathways including, for example, those effecting GRP78; Cell metabolism pathways including, for example, those effecting GFAT-1; Pathways effecting blood vessel growth including, for example, those effecting VEGFA; Pathways effecting triglyceride biosynthesis including, for example, those effecting Agpat6, Fasn, Scd2, or Lpar1; Pathways effecting keratinocytes migration, proliferation and function including, for example, those effecting HIF-1α and IL-1α; Pathways effecting innate immune signaling including, for example, those effecting MyD88, OAS1, S100A7; Pathways effecting cytokine and chemokine expression including, for example, those effecting IL-10, TNF-α, IFN-β, IL-6, IL-1α, IL-23α, IL-15, CCL2, CCL19, IL-12; Pathways effecting antigen presentation including, for example, those effecting Sec22B; CD40, CD70, CD86; Pathways effecting cell migration including, for example, those effecting CCR7; Pathways effecting expression of transgenic antigens including, for example, OVA. In some embodiments, the term "XBP1 pathway upregulating composition" refers herein to any composition that when administered to a keratinocyte results in increased innate immune stimulation, increased cytokine/chemokine expression, increased antigen processing and presentation function including those effecting the production of antigen, and/or increased expression or production of one or more of IL-1α, IL-1β, IFN-β, TNF-α, IL-6, IL-12, IL-15, IL-23a, CCL2, CCL19, MyD88, OAS1, S100A7, Sec22B, CD40, CD70, CD86, CCR7 and HIF-1α in the keratinocyte.

The term "XBP1" refers herein to an X-box binding protein 1 polypeptide also known as Tax-Responsive Element-Binding Protein 5, TREB5, or XBP2, and in humans, is encoded by the XBP1 gene. The term "XBP1 polynucleotide" refers to an XBP1 encoding polynucleotide and includes an XBP1 gene in its entirety or a fragment thereof. In some embodiments, the XBP1 polypeptide or polynucleotide is that identified in one or more publicly available databases as follows: HGNC: 12801; Entrez Gene: 7494; Ensembl: ENSG00000100219; OMIM: 194355; and UniProtKB: P17861. In some embodiments, the XBP1 polynucleotide encodes an XBP1 polypeptide comprising the sequence of SEQ ID NO:1, or a polypeptide sequence having at or greater than about 80%, at or greater than about 85%, at or greater than about 90%, at or greater than about 95%, or at or greater than about 98% homology with SEQ ID NO:1, or a polypeptide comprising a portion of SEQ ID NO:1. The XBP1 polypeptide of SEQ ID NO:1 may represent an immature or pre-processed form of mature XBP1, and accordingly, included herein are mature or processed portions of the XBP1 polypeptide in SEQ ID NO:1. In some embodiments, the XBP1 polynucleotide comprises the sequence of SEQ ID NO:2 or a polynucleotide sequence having at or greater than about 80%, at or greater than about 85%, at or greater than about 90%, at or greater than about 95%, or at or greater than about 98% homology with SEQ ID NO:2, or a polynucleotide comprising a portion of SEQ ID NO:2.

DETAILED DESCRIPTION

Provided herein are compositions and methods for increasing an immune response in a subject, immunizing a subject, and/or treating a disease in a subject that relate to keratinocytes. It is a surprising finding of the present invention that modulation of an XBP1 pathway creates a keratinocyte that is itself an immune modulator, or adjuvant. In some embodiments, the concentration of antigen is increased in the vicinity of the keratinocyte, further increasing the immune response by effector cells within that vicinity. Antigen concentration may be increased via increasing production of the antigen by the keratinocyte itself, increasing production of the antigen by another cell, or by administering the antigen to the vicinity. In some embodiments, an antigen encoding polynucleotide is introduced into the keratinocyte and an XBP1 pathway upregulating composition is administered to the keratinocyte to create a keratinocyte that is an antigen-specific immune modulator. These modified keratinocytes produce extracellular antigen, and in some embodiments, pro-inflammatory mediators that facilitate an antigen-specific immune response by immune effector cells. The modified keratinocytes described herein and the compositions contained therein are useful for increasing immune responses, immunizing and treating diseases in subjects.

More specifically, the results provided in herein demonstrate that transient overexpression of XBP1 locally in the skin microenvironment at the time of antigen delivery induces potent local and systemic immune responses. Novel data is provided that demonstrates that inclusion of plasmid DNA encoding XBP1 in skin results in significantly increased durable $CD8^+$ T cell immune responses to a co-delivered transgenic antigen, and, interestingly, accumulated systemic memory and resident $CD8^+$ T cells in the skin at the immunization site. XBP1's expression in the skin is associated with the induction of a pro-inflammatory cutaneous microenvironment, as evidenced by increased expression of pro-inflammatory cytokines and chemokine, and infiltration of lymphocytes and antigen presenting cells. Further, in the in vitro systems, it is shown herein that XBP1 has a decisive role in promoting keratinocytes to increase the production of co-delivered secreted antigen and one or more of IL-1α, IL-1β, IFN-β, TNF-α, IL-6, IL-12, IL-15, IL-23a, CCL2, CCL19, MyD88, OAS1, S100A7, Sec22B, CD40, CD70, CD86, CCR7 and HIF-1α. The present disclosure therefore describes for the first time that XBP1 may function as a master transcriptional regulator of keratinocytes to enhance the production of secreted vaccine antigens and pro-inflammatory mediators, resulting in a pro-immunogenic skin microenvironment that enables the induction of robust, durable and effective local and systemic antigen-specific immune responses against cancer or infectious diseases.

Accordingly, provided herein are keratinocytes comprising an XBP1 pathway upregulating composition. In some embodiments, the keratinocytes further comprise an antigen polynucleotide. Included herein are keratinocytes at any stage of differentiation, other than corneocytes. In some embodiments, the keratinocyte expresses or overexpresses a keratin-5 polypeptide and a keratin-14 polypeptide. In other embodiments, the keratinocyte expresses or overexpresses a keratin-1 polypeptide and a keratin-10 polypeptide. In still other embodiments, the keratinocyte expresses or overexpresses a keratin-1 polypeptide and a keratin-16 polypeptide. The keratinocytes produce an increased amount of the antigen extracellularly as compared to a control. In some embodiments, the keratinocytes produce an increased amount of one or more pro-inflammatory mediators extracellularly as compared to a control. In one embodiment, the pro-inflammatory mediators are selected from the group of IL-1α, IL-1β, IFN-β, CCL2, IL-15, IL23a, CCL19, and HIF-1α.

In some embodiments, the XBP1 pathway upregulating composition is a vector comprising an XBP1 DNA polynucleotide. Expression of the XBP1 DNA polynucleotide in the keratinocyte results in overexpression of XBP1 polypeptide as compared to a control, and thereby upregulates the XBP1 pathway. Accordingly, included herein are XBP1 DNA polynucleotides, vectors comprising a XBP1 DNA polynucleotide, and keratinocytes comprising such vectors. However, the XBP1 upregulating composition may be any composition that when administered to a keratinocyte, increases or activates a constituent in an XBP1 regulated/responsive pathway. In some embodiments, the XBP1 upregulating composition increases cytokine/chemokine expression, and/or increases antigen processing and presentation function including those effecting the production of antigen, and/or increases expression or production of one or more of and/or increased expression or production of one or more of IL-1α, IL-1β, IFN-β, TNF-α, IL-6, IL-12, IL-15, IL-23a, CCL2, CCL19, MyD88, OAS1, S100A7, Sec22B, CD40, CD70, CD86, CCR7 and HIF-1α in the keratinocytes.

In those embodiments in which the XBP1 pathway upregulating composition is a vector comprising an XBP1 DNA polynucleotide, the vector may also comprise an antigen DNA polynucleotide. Accordingly, provided herein are vectors comprising an XBP1 DNA polynucleotide and an antigen DNA polynucleotide, and keratinocytes comprising such vectors. The antigen DNA polynucleotide may be linked to the same or a different promoter as the XBP1 DNA polynucleotide. In one embodiment, the XBP1 DNA polynucleotide and the antigen DNA polynucleotide are operably linked to the same promoter within the same vector. In other embodiments, the XBP1 DNA polynucleotide and the antigen DNA polynucleotide are operably linked to different promoters. The one or more promoters include, but are not limited to, a cytomegalovirus (CMV) promoter, a K14 (keratin 14) promoter, and a CD11c promoter. However, it should be understood that the present invention is not limited to the use of a specific promoter. Any promoter that achieves expression of the XBP1 DNA polynucleotide within a keratinocyte and/or the antigen DNA polynucleotide within a relevant mammalian cell is within the scope of this invention. In other embodiments, the XBP1 DNA polynucleotide and the antigen DNA polynucleotide are contained within different vectors.

In some embodiments, the XBP1 polynucleotide encodes an XBP1 polypeptide comprising SEQ ID NO:1 or a homolog or fragment thereof. In some embodiments, the XBP1 polynucleotide comprises SEQ ID NO:2 or a homolog or fragment thereof. The antigen polynucleotide of the present invention can be any one known to those of skill in the art. In some embodiments, the antigen polynucleotide encodes a viral antigen. In other embodiments, the antigen polynucleotide encodes a cancer-related antigen. In still other embodiments, the antigen polynucleotide encodes a bacterial antigen.

In other embodiments, the XBP1 upregulating composition affects another constituent in the XBP1 pathway such as downstream effectors of XBP1 including those of the ER stress Gene Network including, for example, Sec24c, Sec31a, Sec23b, Sec24d, Sec61a1, Copg1, Copb2, Gosr2, Golgb1, Golga3, Arfgap3, Rpn2, Spcs3, Fasn, Hspa13, Surf4, Jnk, Mfn2, Atf6, Dnajc3, Pdia6, Pdia5, Pdia4, Rpn1, Os9, Hyou1, Csdc47, Stt3a, and Nlrx1. Other downstream pathways known to be effected by XBP1 include: Protein transport pathways including, for example, those effecting GRP78; Cell metabolism pathways including, for example, those effecting GFAT-1; Pathways effecting blood vessel growth including, for example, those effecting VEGFA; Pathways effecting triglyceride biosynthesis including, for example, those effecting Agpat6, Fasn, Scd2, or Lpar1; Pathways effecting innate immune signaling including, for example, those effecting MyD88, OAS1; Pathways effecting cytokine expression including, for example, those effecting IL-1β, TNF-α, IFN-β, IL-6, IL-1α, IL-15, CCL2, IL-12; Pathways effecting antigen presentation including, for example, those effecting Sec22B; CD40, CD70, CD86; Pathways effecting cell migration including, for example, those effecting CCR7; Pathways effecting expression of transgenic antigens including, for example, OVA.

Also provided herein are methods of treating or increasing an immune response in a subject by administering to a keratinocyte a pharmaceutically effective amount of one or more compositions comprising an XBP1 pathway upregulating composition, wherein the keratinocyte is in the subject or administered to the subject. In these methods, the XBP1 pathway upregulating composition, and ultimately the keratinocyte, functions as an adjuvant to increase an immune response in the subject. The XBP1 pathway upregulating composition and the keratinocyte used in the methods may be any as described above and below. In some embodiments, the XBP1 pathway upregulating composition is administered to keratinocytes within the skin of the subject via a cutaneous, or transdermal administration. In other embodiments, the XBP1 pathway upregulating composition is administered to keratinocytes ex vivo, and the keratinocytes are then administered to the subject via a form of adoptive cell therapy.

In some embodiments, the method further comprises administering a pharmaceutically effective amount of an antigen to the subject. In these embodiments, the immune response to the antigen is increased, and therefore, these embodiments include methods of immunizing the subject to the antigen. The antigen may be administered before, after or at the same time as the XBP1 pathway upregulating composition or keratinocyte comprising the XBP1 pathway upregulating composition. As described herein, the antigen may be, but is not limited to, a polypeptide, an oligonucleotide, and a polysaccharide. The antigen may be administered via any means as described herein, and in some embodiments, is administered via a cutaneous, or transdermal administration. In some embodiments, the antigen is administered to a site near or within the vicinity of the keratinocyte.

In some embodiments, an antigen polynucleotide is administered to the keratinocyte. Accordingly, provided herein are methods of immunizing or treating a subject by administering to a keratinocyte a pharmaceutically effective amount of one or more compositions comprising an antigen polynucleotide and an XBP1 pathway upregulating composition, wherein the keratinocyte is in the subject or administered to the subject. In some embodiments, the antigen polynucleotide and the XBP1 pathway upregulating polynucleotide are administered to keratinocytes within the skin of the subject via a cutaneous, or transdermal administration. In other embodiments, the XBP1 pathway upregulating composition and the antigen polynucleotide are administered to keratinocytes ex vivo, and the keratinocytes are then administered to the subject via a form of adoptive cell therapy.

Administration of the antigen polynucleotide and an XBP1 pathway upregulating composition to the subject results in an immune response in the subject that is specific for the antigen. The antigen specific immune response is mediated, at least in part, by $CD8^+$ T cells. It is believed that, upon production of the antigen by the keratinocyte, antigen presenting cells present the antigen to $CD8^+$ T cells, thus initiating a $CD8^+$ T cell antigen specific immune response. Any concomitant production of pro-inflammatory mediators by the keratinocyte facilitate this process. In some embodiments, antigen-specific IFN-γ- and Granzyme B-expressing $CD8^+$ T cells are increased locally or systemically in response to the administration. In other or further embodiments, $CD103^+CD8^+$ memory T cells are increased locally or systemically in response to the administration. Since the methods described herein result in both effector and memory T cell responses, the methods of the present invention include use of the compositions described herein for both treatment and immunization.

Treatments according to the invention may be applied preventively, prophylactically, palliatively or remedially. Prophylactic treatments are administered to a subject prior to onset (e.g., before obvious signs of disease or cancer), during early onset (e.g., upon initial signs and symptoms of disease or cancer), or after an established development of a disease or cancer. Prophylactic administration can occur for several days to years prior to the manifestation of symptoms of the disease or cancer. In some instances, the terms "treat," "treating," "treatment" and grammatical variations thereof, include partially or completely reducing the size of a solid tumor or a cancerous lesion or reducing the number of solid tumors or cancerous lesions as compared with prior to treatment of the subject or as compared with the incidence of such symptom in a general or study population. Accordingly, the methods of treatment may comprise adoptive cell therapies (ACT) or vaccination therapies.

Included herein is a medicament for increasing an immune response in a subject in need thereof, comprising a pharmaceutically effective amount of a composition comprising an XBP1 pathway upregulating composition. Further included is a medicament for treating a viral infection, a bacterial infection or a cancer in a subject, comprising a pharmaceutically effective amount of a composition comprising an XBP1 pathway upregulating composition. Still further included herein is a use of an XBP1 pathway upregulating composition in the manufacture of a medicament for the treatment of a viral infection, a bacterial infection or a cancer. In each of these embodiments, the XBP1 pathway upregulating composition can be as described above and below. In some embodiments, the medicament further comprises an antigen. The antigen can be any as described above and below.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1: XBP1 Enhances the Production of Secreted Vaccine Antigen and Pro-Inflammatory Cytokines by Keratinocytes Pam 212 (a mouse keratinocyte cell line) cells ($5$-$6 \times 10^4$) were cultured overnight in 1 ml DMEM supplemental with 10% FBS, glutamine (2 mM) and 1× antibiotic antimycotic solution and then untreated or transiently co-transfected by plasmid DNA encoding Ova and XBP1 (or control vector pcDNA3.1+) using the TransIT®-Keratinocyte Transfection Reagent (Mirus) according to vendor's instruction. After 3 days, Ova in the culture supernatants were measured by ELISA (USCN life science Inc., Hölzel Diganostik, Germany). The results are shown in FIG. 1a.

FIG. 1(B-D) further shows that XBP1 enhances the production of pro-inflammatory cytokines and chemokines by keratinocytes. Experiments were performed as described in relation to FIG. 1A. After 3 days of transfection, IL-1α, IFN-β and CCL2 in the culture supernatants were measured by ELISA. Data from four independent experiments are shown in FIG. 1(B-D) and were statistically analyzed (Student's t test). *$P<0.05$; **$P<0.01$. Notably, in all cases, co-transfection of the dominant-negative XBP1, dnXBP1, which specifically inhibits XBP1s without affecting cell viability or growth abrogated these XBP1s overexpression effects.

Example 2: XBP1 Promotes Lymphocyte and $CD11c^+$ Cell Infiltration into Skin C57BL/6 (B6) mice (6-8 weeks, female) were untreated or immunized with OVA plus control vector DNA or OVA plus XBP1 DNA. 3 days later, skin at the immunization site was removed and cut into small pieces and subsequently incubated with Collagenase D (1 mg/ml) and DNase (1 mg/ml) in IMDM for 1 hour in an incubator, and then mashed and passed through a 70 μm cell strainer. Single-cell suspensions of skin tissues were pre-incubated on ice with Fc Block (BD Bioscience) for 15 minutes and then stained with Fixable Viability Dye EFLUOR® 780, anti-mouse CD45-APC and CD11c-PE-Cy7 and analyzed by flow cytometry using a BD LSRII flow cytometer (BD Biosciences) and analyzed using FlowJo software (v9.2, Tree Star). One representative of three independent experiments showing CD45$^+$ (FIG. 2A, C, E) or CD11c$^+$ cells (FIG. 2B, D, F) among total live skin cells is presented in FIG. 2.

Example 3: XBP1 Overexpression Increases the Expression of Pro-Inflammatory Cytokines and Chemokines in the Skin Immunized skin was obtained as described in Example 2. Total RNA was purified from homogenized skin using TRI REAGENT® (Sigma). RNA was quantified by Nanodrop (Thermo Scientific). The cDNA was synthesized from mRNA using The QIAGEN One-Step RT-PCR Kit with gDNA wipeout. Subsequently, TAQMAN® Assay-based real-time PCR was performed in an Applied Biosystems StepOnePlus™ Instrument following standard protocols with primers purchased from IDT DNA for each gene. Mouse β-actin was a control. Relative mRNA expression was determined and normalized based on the $2^{-\Delta\Delta Ct}$ method. Data represent three mice from each group and were statistically analyzed. The results are shown in FIG. 3(A-F).

Example 4: XBP1 Overexpression Enables Induction of Durable Systemic Antigen-Specific IFN-γ- and Granzyme B-Expressing CD8$^+$ T Cell Immunity B6 mice were untreated or immunized once as described in Example 3. 6-7 weeks later, single-cell suspensions (3×10$^6$) of splenocytes and vaccine/skin dLN) were restimulated with OVA-specific MHC I peptides (SIINFEKL) (or irrelevant β-gal MHC I peptides: DAPIYTNV) (2 μg/ml) in 2 ml RPMI 1640 10% FBS for 3-4 days. IFN-γ in the culture supernatants was determined by ELISA. Granzyme B was measured by surface staining of anti-mouse CD8-Alexa flour 700 and subsequently intracellular staining of anti-mouse granzyme B-Alexa-647 and analyzed by flow cytometry using a BD LSRII flow cytometer and analyzed using FlowJo software. One representative of three independent experiments showing Granzyme B expression in gated CD8$^+$ T cells is presented in FIG. 4(A-E).

Example 5: XBP1 Promotes the Accumulation of Memory [Central (CD44$^+$CD62L$^+$) and Effector (CD44$^+$CD62L$^-$)] CD8$^+$ T Cells and Skin-Resident CD103$^+$CD8$^+$ Memory T Cells in Skin at the Immunization Site Mice were immunized as described in Example 4. 6-7 weeks later, single-cell suspensions from skin at the immunization site were prepared as described in Example 2, and subsequently pre-incubated on ice with Fc Block for 15 minutes and then stained with Fixable Viability Dye EFLUOR® 450 (dead cells were excluded from analysis), anti-mouse CD45-APC, CD8-PE-Cy7, CD44-FITC, CD62L-percep5.5, CD103-PE, and analyzed by flow cytometry using a BD LSRII flow cytometer and analyzed using FlowJo software. One representative of 3 experiments showing CD44$^+$CD62L$^+$ and CD44$^+$CD62L$^-$ in gated CD8$^+$ T cells or CD103$^+$CD8$^+$ T cells in gated total live skin cells is shown in FIG. 5.

Example 6: XBP1 Increases Pro-Inflammatory Cytokines and Chemokines in Human Skin In Situ Human skin epidermal/dermal explants were left untreated or immunized with human XBP1 or control vector and cultured. 72 hours later, skin at the immunization site was used for RNA extraction. Relative expression of various genes was determined by real-time qRT-PCR and normalized based on the $2^{-\Delta\Delta Ct}$ method. The human B2M housekeeping gene served as an internal control.

Data from three experiments using three different human skin explants is presented individually in FIG. 6(A-O), which shows increased expression of XBP1, GRP78, GFAT-1, VEGFA, HIF-1α, IL-1β, MyD88, IL-23α, OAS1, S100A7, TNF-α, CCL19, CD86, IL-15, and OVA.

Figure 7:
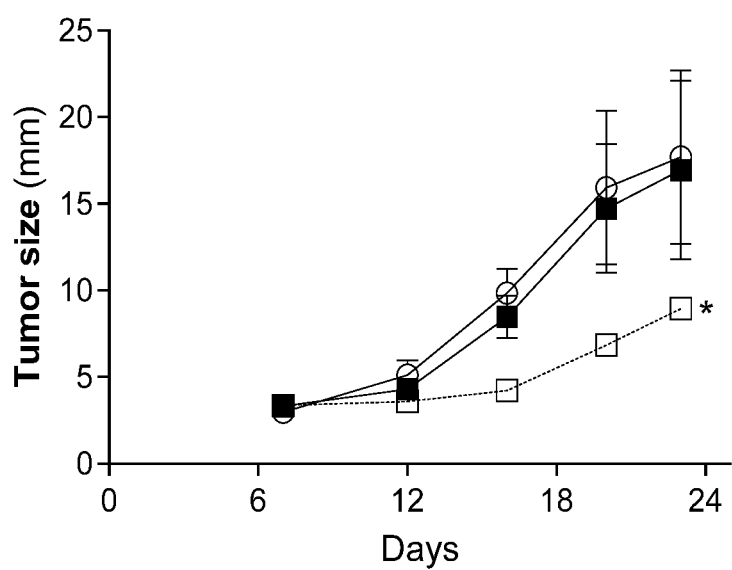
FIG. 7 contains a graph showing that transient overexpression of XBP1 in skin drives vaccine-induced durable protective immunity. Untreated (filled squares), control vector plus OVA (open circles), XBP1 plus OVA (open squares).

Example 7: Transient Overexpression of XBP1s in Skin Drives Vaccine-Induced Durable Protective Immunity B6 mice (4/group) were untreated or immunized once as in Example 4. 5 months later, mice were i.d. challenged with exponentially growing B16-OVA (1×10$^5$). Melanoma growth was monitored and data were statistically analyzed (9). *P<0.05. The results are shown in FIG. 7.

---

The invention claimed is:

1. A method of increasing an immune response in a human subject in need thereof, comprising administering to a keratinocyte a pharmaceutically effective amount of a composition comprising a human XBP1 polynucleotide and an antigen polynucleotide, wherein the keratinocyte is in the subject or administered to the subject, the XBP1 polynucleotide and the antigen polynucleotide are expressed in the keratinocyte, secretion of the antigen from the keratinocyte is increased as compared to a control and the immune response is increased in the subject.

2. The method of claim 1, wherein the subject has a skin infection or a skin cancer.

3. The method of claim 1, further comprising administering a pharmaceutically effective amount of the antigen to the subject.

4. The method of claim 1, wherein the antigen is a bacterial antigen.

5. The method of claim 1, wherein the antigen is a viral antigen.

6. The method of claim 1, wherein the antigen is a cancer-related antigen.

7. The method of claim 1, wherein a vector comprising the XBP1 polynucleotide is administered to the subject.

8. The method of claim 7, wherein the XBP1 polynucleotide encodes a polypeptide comprising SEQ ID NO:1 or a homolog thereof.

9. The method of claim 7, wherein the XBP1 polynucleotide comprises SEQ ID NO:2.

10. The method of claim 7, wherein the vector further comprises the antigen polynucleotide.

11. The method of claim 1, wherein the subject is treated prophylactically.

12. The method of claim 1, wherein administration is cutaneous or transdermal.

13. A polynucleotide comprising an XBP1 polynucleotide operably linked to a K14 promoter and an antigen polynucleotide operably linked to a promoter.

14. A vector comprising the polynucleotide sequence of claim 13.

15. A keratinocyte comprising the polynucleotide sequence of claim 13.

16. The keratinocyte of claim 15, wherein the keratinocyte has increased expression of one or more of IL-1α, IL-1β, IFN-β, CCL2, IL-15, IL23a, CCL19, HIF-1α GRP78, GFAT-1, TNF-α, VEGFA, HIF-1α, OAS1, S100A7, and CD86.

17. A method of treating a viral infection, a bacterial infection or a cancer in a human subject, comprising administering to a keratinocyte a pharmaceutically effective amount of a composition comprising a human XBP1 polynucleotide and an antigen polynucleotide, wherein the keratinocyte is in the subject or administered to the subject, the XBP1 polynucleotide and the antigen polynucleotide are expressed in the keratinocyte, and secretion of the antigen from the keratinocyte is increased as compared to a control.

18. The method of claim 17, wherein a vector comprising an XBP1 polynucleotide and the antigen polynucleotide is administered to the subject.

19. The method of claim 18, wherein the XBP1 polynucleotide encodes a polypeptide comprising SEQ ID NO: 1 or a homolog thereof.

20. The method of claim 1, wherein the increased immune response is antigen-specific.

21. The method of claim 20, wherein there is no immune response to an XBP1 polypeptide.

* * * * *

UNITED STATES PATENT AND TRADEMARK OFFICE
CERTIFICATE OF CORRECTION

PATENT NO. : 12,201,687 B2
APPLICATION NO. : 17/558977
DATED : January 21, 2025
INVENTOR(S) : Louis D. Falo, Jr. and Zhaoyang You Page 1 of 1

It is certified that error appears in the above-identified patent and that said Letters Patent is hereby corrected as shown below:

In the Claims

In Claim 16, Column 18, Lines 41-42, delete "HIF-1αGRP78," and insert -- HIF-1α, GRP78, --.

Signed and Sealed this
Twenty-ninth Day of April, 2025

Coke Morgan Stewart
*Acting Director of the United States Patent and Trademark Office*

SEQUENCE LISTING

```
<160> NUMBER OF SEQ ID NOS: 2

<210> SEQ ID NO 1
<211> LENGTH: 371
<212> TYPE: PRT
<213> ORGANISM: Homo sapiens

<400> SEQUENCE: 1

Met Val Val Val Ala Ala Ala Pro Ser Ala Ala Thr Ala Ala Pro Lys
1               5                   10                  15

Val Leu Leu Leu Ser Gly Gln Pro Ala Ser Gly Gly Arg Ala Leu Pro
            20                  25                  30

Leu Met Val Pro Gly Pro Arg Ala Ala Gly Ser Glu Ala Ser Gly Thr
```

```
                    35                  40                  45
Pro Gln Ala Arg Lys Arg Gln Arg Leu Thr His Leu Ser Pro Glu Glu
         50                  55                  60
Lys Ala Leu Arg Arg Lys Leu Lys Asn Arg Val Ala Ala Gln Thr Ala
 65                  70                  75                  80
Arg Asp Arg Lys Lys Ala Arg Met Ser Glu Leu Glu Gln Gln Val Val
                 85                  90                  95
Asp Leu Glu Glu Glu Asn His Lys Leu Gln Leu Glu Asn Gln Leu Leu
            100                 105                 110
Arg Glu Lys Thr His Gly Leu Val Val Glu Asn Gln Glu Leu Arg Thr
        115                 120                 125
Arg Leu Gly Met Asp Thr Leu Asp Pro Asp Glu Val Pro Glu Val Glu
    130                 135                 140
Ala Lys Gly Ser Gly Val Arg Leu Val Ala Gly Ser Ala Glu Ser Ala
145                 150                 155                 160
Ala Gly Ala Gly Pro Val Val Thr Ser Pro Glu His Leu Pro Met Asp
                165                 170                 175
Ser Asp Thr Val Ala Ser Ser Asp Ser Glu Ser Asp Ile Leu Leu Gly
            180                 185                 190
Ile Leu Asp Lys Leu Asp Pro Val Met Phe Phe Lys Cys Pro Ser Pro
        195                 200                 205
Glu Ser Ala Ser Leu Glu Glu Leu Pro Glu Val Tyr Pro Glu Gly Pro
    210                 215                 220
Ser Ser Leu Pro Ala Ser Leu Ser Leu Ser Val Gly Thr Ser Ser Ala
225                 230                 235                 240
Lys Leu Glu Ala Ile Asn Glu Leu Ile Arg Phe Asp His Val Tyr Thr
                245                 250                 255
Lys Pro Leu Val Leu Glu Ile Pro Ser Glu Thr Glu Ser Gln Thr Asn
            260                 265                 270
Val Val Val Lys Ile Glu Glu Ala Pro Leu Ser Ser Ser Glu Glu Asp
        275                 280                 285
His Pro Glu Phe Ile Val Ser Val Lys Lys Glu Pro Leu Glu Asp Asp
    290                 295                 300
Phe Ile Pro Glu Leu Gly Ile Ser Asn Leu Leu Ser Ser Ser His Cys
305                 310                 315                 320
Leu Arg Pro Pro Ser Cys Leu Leu Asp Ala His Ser Asp Cys Gly Tyr
                325                 330                 335
Glu Gly Ser Pro Ser Pro Phe Ser Asp Met Ser Ser Pro Leu Gly Thr
            340                 345                 350
Asp His Ser Trp Glu Asp Thr Phe Ala Asn Glu Leu Phe Pro Gln Leu
        355                 360                 365
Ile Ser Val
    370

<210> SEQ ID NO 2
<211> LENGTH: 1116
<212> TYPE: DNA
<213> ORGANISM: Homo sapiens

<400> SEQUENCE: 2
atggtggtgg tggcagcggc gccgagcgcg gccacggcgg cccccaaagt gctactctta      60
tctggccagc ccgcctccgg cggcggggcg ctgccgctca tggtacccgg tccgcgggca     120
gcagggtcgg aggcgagcgg gacaccgcag gctcgcaagc ggcagcggct cacgcacctg     180
```

```
agcccggagg agaaagcgct gcggaggaaa ctgaaaaaca gagtagcagc gcagactgct    240
cgagatagaa agaaagcccg gatgagcgag ctggagcagc aagtggtgga tttggaagaa    300
gagaaccaca aactccagct agaaaatcag cttttacggg agaaaactca cggccttgtg    360
gttgagaacc aggagttaag aacacgcttg ggaatggaca cgctggatcc tgacgaggtt    420
ccagaggtgg aggccaaggg gagtggagta aggctggtgg ccgggtctgc tgagtccgca    480
gcaggtgcag gcccagttgt cacctcccca gaacatcttc ccatggactc tgacactgtt    540
gcctcttcag attctgagtc tgatatcctt ttgggcattc tggacaagtt ggaccctgtc    600 atgttttca aatgtccttc cccagagtct gctagtctgg aggaactccc agaggtctac    660
ccagaaggac ctagttcctt accagcctcc ctttctctgt cagtggggac ctcatcagcc    720
aagctggaag ccattaatga actcattcgt tttgaccatg tataccaa gcctctagtt     780 ttagagatcc cctctgagac agagagtcaa actaacgtgg tagtgaaaat tgaggaagca    840
cctctaagct cttcagaaga ggatcaccct gaattcattg tctcagtgaa gaaagagcct    900
ttggaagatg acttcatccc agagctgggc atctcaaacc tgctttcatc cagccattgt    960
ctgagaccac cttcttgcct gctggacgct cacagtgact gtggatatga gggctcccct   1020
tctcccttca gtgacatgtc ttctccactt ggtacagacc actcctggga ggatactttt   1080
gccaatgaac ttttccccca gctgattagt gtctaa                             1116
```